United States Patent [19]

Jarvis

[11] 4,112,124

[45] Sep. 5, 1978

[54] FOOD PACKAGING SYSTEM AND METHOD

[75] Inventor: Alexander S. Jarvis, Montreal, Canada

[73] Assignee: Drisan Packaging Ltd., Toronto, Canada

[21] Appl. No.: 137,553

[22] Filed: Apr. 26, 1971

[51] Int. Cl.$^2$ .................... B65B 55/16; B65B 55/18
[52] U.S. Cl. .................................. 426/234; 426/107;
426/410; 53/434; 53/512
[58] Field of Search .............. 99/218, 214, 189, 249; 53/22 B, 112 B, 86, 91, 92, 93, 95; 21/DIG. 2, 78, 80; 250/52; 426/234, 410

[56] References Cited

U.S. PATENT DOCUMENTS

| | | | |
|---|---|---|---|
| 1,182,213 | 5/1916 | Ryan | 99/218 UX |
| 1,770,435 | 7/1930 | Seltzer | 53/95 X |
| 2,095,502 | 10/1937 | Johnston | 250/52 X |
| 2,204,131 | 6/1940 | Glunz | 99/218 |
| 2,231,935 | 2/1941 | McCutchen | 250/52 |
| 2,401,131 | 5/1946 | Bensel | 99/218 X |
| 2,425,816 | 8/1947 | Maxson | 99/218 X |
| 2,649,671 | 8/1953 | Bartelt | 99/189 UX |
| 2,824,014 | 2/1958 | Sperti | 99/218 |
| 2,906,104 | 9/1959 | Schaefer et al. | 99/218 X |
| 2,965,494 | 12/1960 | Williams | 99/189 X |
| 3,091,901 | 6/1963 | Silverstolpe | 53/86 X |
| 3,483,005 | 12/1969 | Urbain | 99/214 |
| 3,619,975 | 11/1971 | Johnson et al. | 53/112 B |

*Primary Examiner*—Steven L. Weinstein
*Attorney, Agent, or Firm*—Lowe, King, Price & Markva

[57] ABSTRACT

Disclosed are a method of and system for packaging commercially sterile foods by placing the sterile food in a plastic container tending towards opacity to visible light radiation and tending towards transparency to ultraviolet radiation. The container is open and the food product is cooled to a temperature slightly above the freezing point of water preparatory to and while in a chamber having an atmosphere of cooled, dry inert, sterile gas. In the chamber, the inert gas and food product are irradiated by ultraviolet energy that propagates through the container. The container is sealed in the chamber, whereby the inert atmosphere is maintained on the surface of the food product while stored in the container, at temperatures slightly above the freezing point of water for prolonged time periods.

14 Claims, 15 Drawing Figures

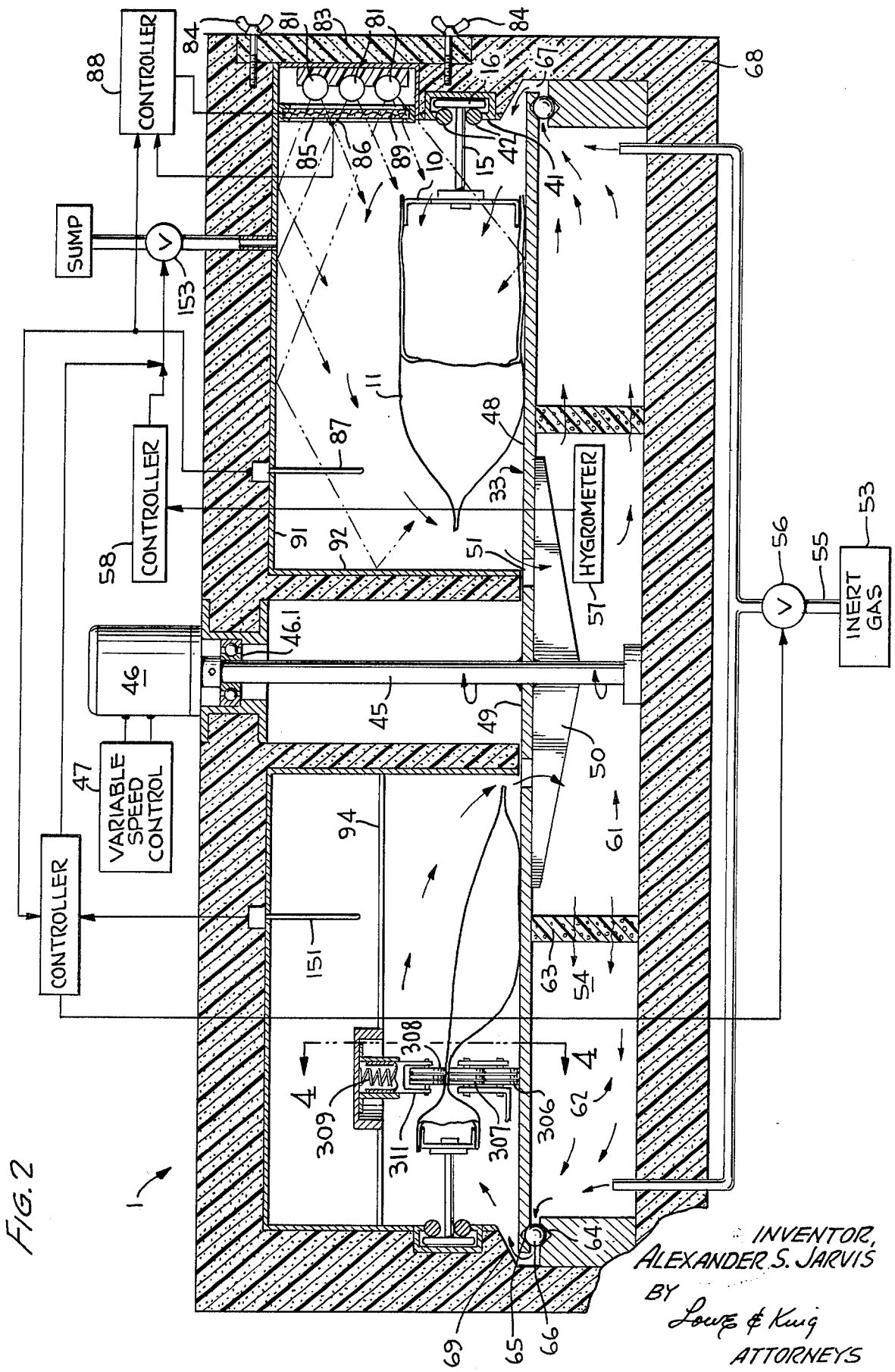

INVENTOR,
ALEXANDER S. JARVIS
BY Lowe & King
ATTORNEYS

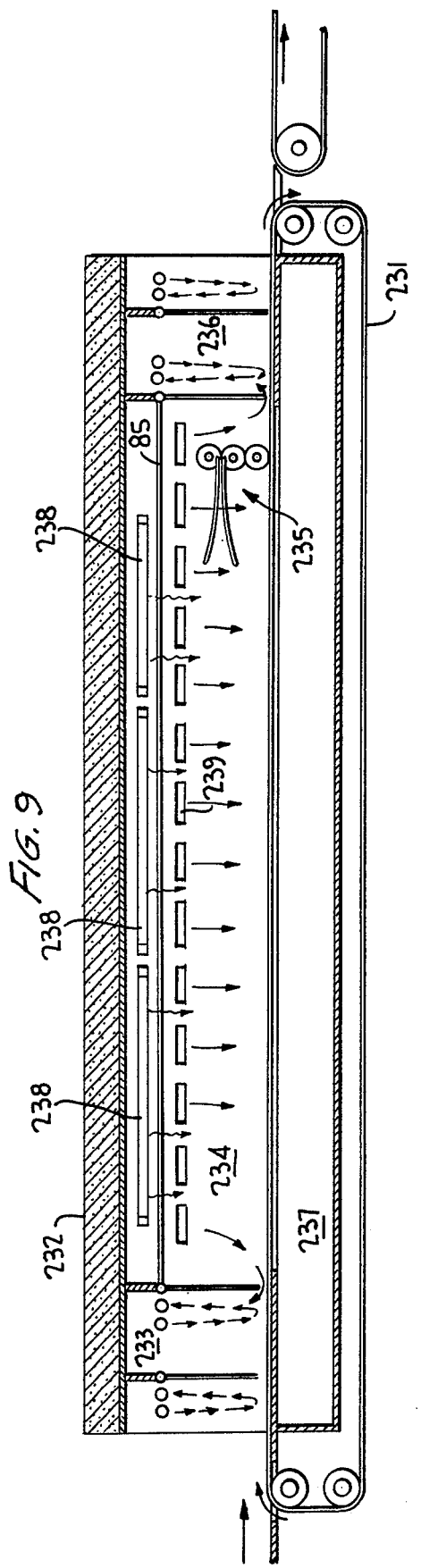
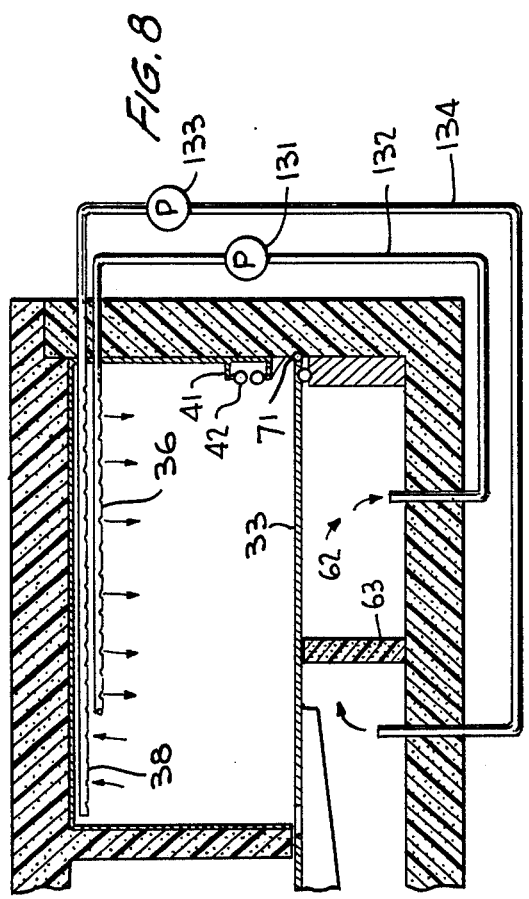

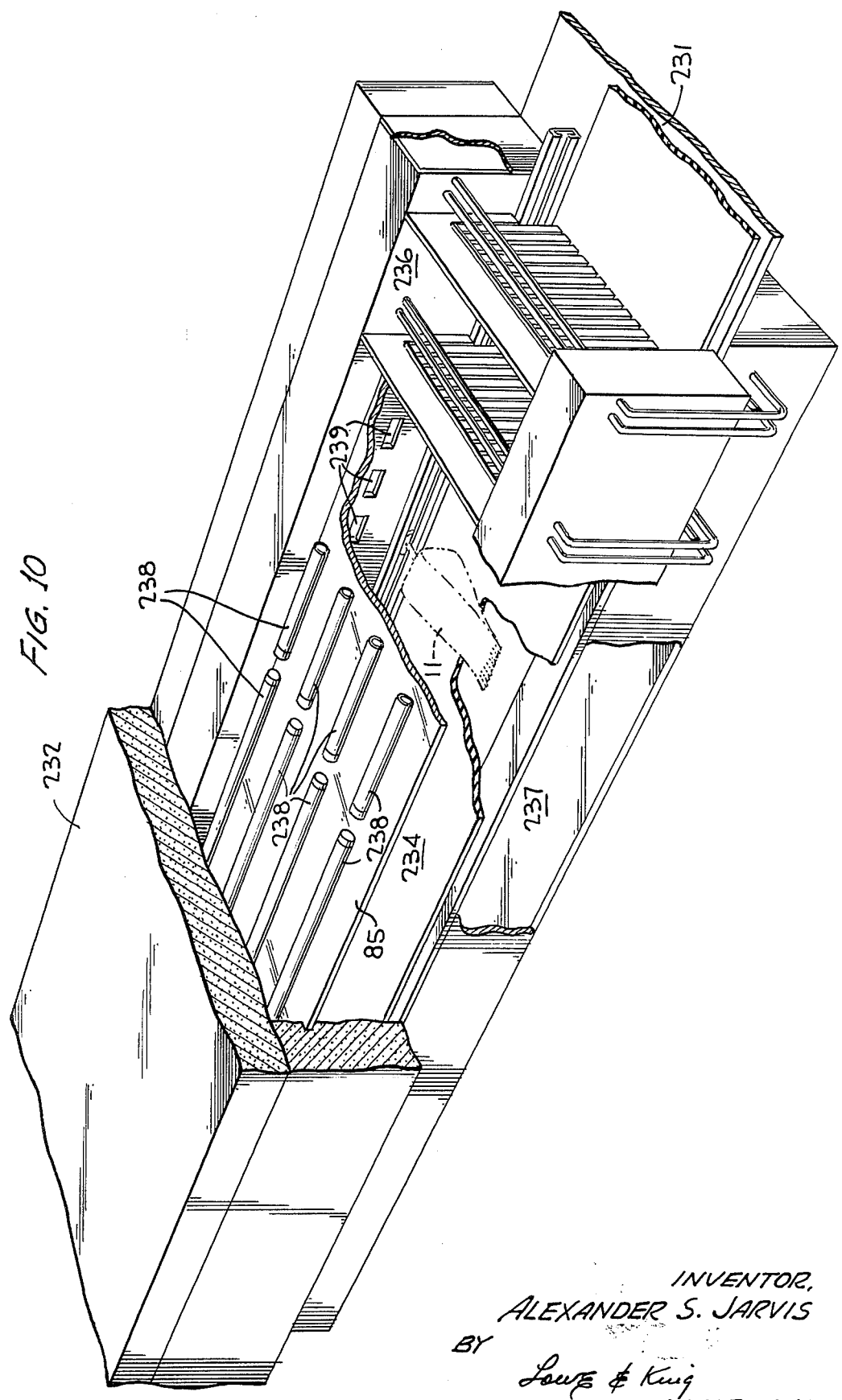

FOOD PACKAGING SYSTEM AND METHOD

The present invention relates generally to systems for and methods of packaging food products, and, more particularly to a food packaging process and apparatus wherein the food product is sterilized by ultraviolet radiation while in an inert gas atmosphere that surrounds the food after packaging has been completed.

Presently existing techniques and machines for packaging food which enable the food to be maintained in a sterile condition for prolonged time periods generally involve freezing of the food product and maintenance of the freezing condition throughout the storage period. The freezing process, however, causes a breakdown of cells within the food product which frequently results in loss of flavor of the food product. In addition, once a food product has been frozen, it should not thaw and be refrozen because of further cell breakdown and the revivifying of bacteria and stimulation of their growth that occur in the unfrozen state, which can cause deleterious effects to the health of the consumer. Techniques for storing food products for extended time periods at temperatures greater than freezing have not generally been employed because oxygenous decomposition of the food through exposure to atmospheric air causes loss of flavor as well as color, in addition to changes in weight of the food product. Further, many foods when refrigerated slightly above the freezing point of water have a tendency to decompose and lose sterility.

In accordance with the present invention, there is provided a system for and method of packaging commercially sterile foods in such a manner that the food product can be maintained at normal refrigerator temperatures, slightly above freezing (approximately 36° F.) for extended time periods of several months. The food products can be stored in an air impervious container at normal refrigerator without deterioration of the food product or decomposition because the food product surface is sterilized during packaging by being irradiated with ultraviolet radiation. In addition, during the packaging operation, the food product is contacted with an inert, dry, sterile gas, such as nitrogen or carbon dioxide. The inert gas fills the container during a sealing operation, whereby the sterile surface of the food product is maintained during storage at nonfreezing refrigerator temperatures.

While the steps of irradiating a food product with ultraviolet energy for sterilization and packaging in an inert atmosphere are disclosed in the prior art separately, the combination of the steps produces a synergistic result. It has been found that certain deleterious colonies of bacteria are introduced in a commercially sterile food product between the time of product removal from an oven and packaging during apportionment and normal handling. In accordance with the present invention these and possibly other colonies actually decrease in number at the same time that their further growth is inhibited by the combination of the ultraviolet radiation and encapsulation or packaging with the inert gas. If the food product is irradiated with ultraviolet radiation to the exclusion of being packaged with an inert gas or the product is packaged with an inert gas but not irradiated, these colonies of bacteria do not decrease in number but are initially stabilized in number and then, after a relatively short time period, commence growing.

In accordance with one aspect of the present invention the ultraviolet irradiation and inert gas contacting of the food product are performed at the same time in a chamber filled with the inert gas and containing a sterilizing ultraviolet field. The ultraviolet field, in addition to sterilizing the food product, sterilizes the inert gas. Thereby, bacteria that might be present in the inert gas are killed and do not have an opportunity to alight on and contaminate the food product.

A feature of the invention is that the food products are preferably placed in a container that tends towards opacity to visible light radiation and tends towards transparency to ultraviolet radiation whereby the food products are sterilized by the ultraviolet field while in the container. The container tends towards opacity to visible light radiation because visible light radiation stimulates the growth of bacteria through the action of necrohormones, hormones that are produced by bacteria while they are in the dying process and which enhance the reproduction capabilities of remaining bacteria. It is important to decrease the action of necrohormones because they promote the growth of the remaining bacteria colonies. The use of ultraviolet radiation during the packaging operation effectively kills or renders inert bacteria content on the surface of the food product.

In accordance with another feature of the invention, the inert gas is maintained in a chamber having entrance and exit locations sealed by gas curtains. The gas curtains effectively isolate the interior of the chamber from the outside atmosphere since the gas used in the curtains is the same inert gas as is utilized in the interior of the chamber. Since the food product is preferably inserted in an open, flexible container prior to entering the chamber, the gas curtain at the chamber entrance compresses the container to force some of the atmospheric air in the container through the opening thereof. Thereby, when the container reaches the interior of the chamber the inert gas, which is maintained at a pressure slightly greater than atmospheric, quickly displaces atmospheric air in the container and more readily fills the entire interior of the container, thereby assuring more positive contact between the surface of the food product and the inert gas.

Still another feature of the invention involves substantially preventing ultraviolet radiation from escaping from the interior of the chamber while allowing food products to pass through it. This is accomplished by providing an isolation chamber having a pair of ultraviolet absorbing gates through which the food product and container pass. The two gates of the isolation chamber are displaced from each other by a sufficient distance to enable normal size food product containers to be located between them so that at least one of the gates is always closed and possibly harmful ultraviolet radiation cannot escape from the interior of the chamber. In response to both of the gates being simultaneously open, a conveyor carrying the food product container is stopped and the ultraviolet source is deactivated.

In accordance with another aspect of the invention, the ultraviolet source is in the form of a plurality of elongated tubes or lamps which are placed in a container having an ultraviolet transparent window that forms one wall of the chamber. The window may be cooler than the inert gas in the chamber so that there is a tendency for water particles in the gas to condense on the window. Water condensation on the window absorbs the ultraviolet radiation and must be eliminated if desired sterility is to be attained. To this end, a controller is provided for eliminating the condensation by heating the window so that it is always maintained at a temperature greater than the inert gas atmosphere in the chamber.

It is, accordingly, an object of the present invention to provide a new and improved system for and method of packaging food products.

Another object of the invention is to provide a new and improved system for and method of packaging food products wherein the products may be stored for prolonged time periods at normal, nonfreezing refrigerator temperatures without deleterious effects on the product.

An additional object of the invention is to provide a new and improved system for and method of packaging food products wherein the number of colonies of bacteria in a product is reduced at the same time as further growth of the bacteria is inhibited even after the packaging operation has been performed.

Still another object of the invention is to provide a new and improved system for and method of packaging food products wherein the stimulation of bacteria growth through the action of necrohormones is substantially precluded.

Yet another object of the present invention is to provide a new and improved system for and method of packaging food products in such a manner that they may be refrigerated at nonfreezing temperatures for extended periods of several months with no deterioration of food product caused through loss of flavor or color, or change in weight caused by oxygenous decomposition through exposure to atmospheric oxygen.

Yet another object of the invention is to provide a system for and method of packaging a food product wherein the product is sterilized by irradiation by ultraviolet energy and is contacted with an inert gaseous atmosphere during the sterilization and packaging operations.

Another object of the present invention is to provide a system for irradiating a food product with ultraviolet energy in a chamber filled with inert, cooled gas that is sterilized by the same ultraviolet energy that irradiates the product.

Another object of the present invention is to provide a system for irradiating a food product with ultraviolet energy in a chamber filled with inert, cooled gas, wherein tendencies for condensation on windows for transmitting the ultraviolet radiation to the chamber are precluded.

Yet another object of the present invention is to provide a new and improved system for feeding a flexible container of food packages into an inert gas atmosphere within a chamber, wherein gases within the container have a tendency to be expelled as the container is being introduced into the chamber.

The above and still further objects, features and advantages of the present invention will become apparent upon consideration of the following detailed description of several specific embodiments thereof, especially when taken in conjunction with the accompanying drawings, wherein:

FIG. 2 is a side view of the apparatus illustrated in FIG. 1, taken through the line 2—2;

Figure 1:
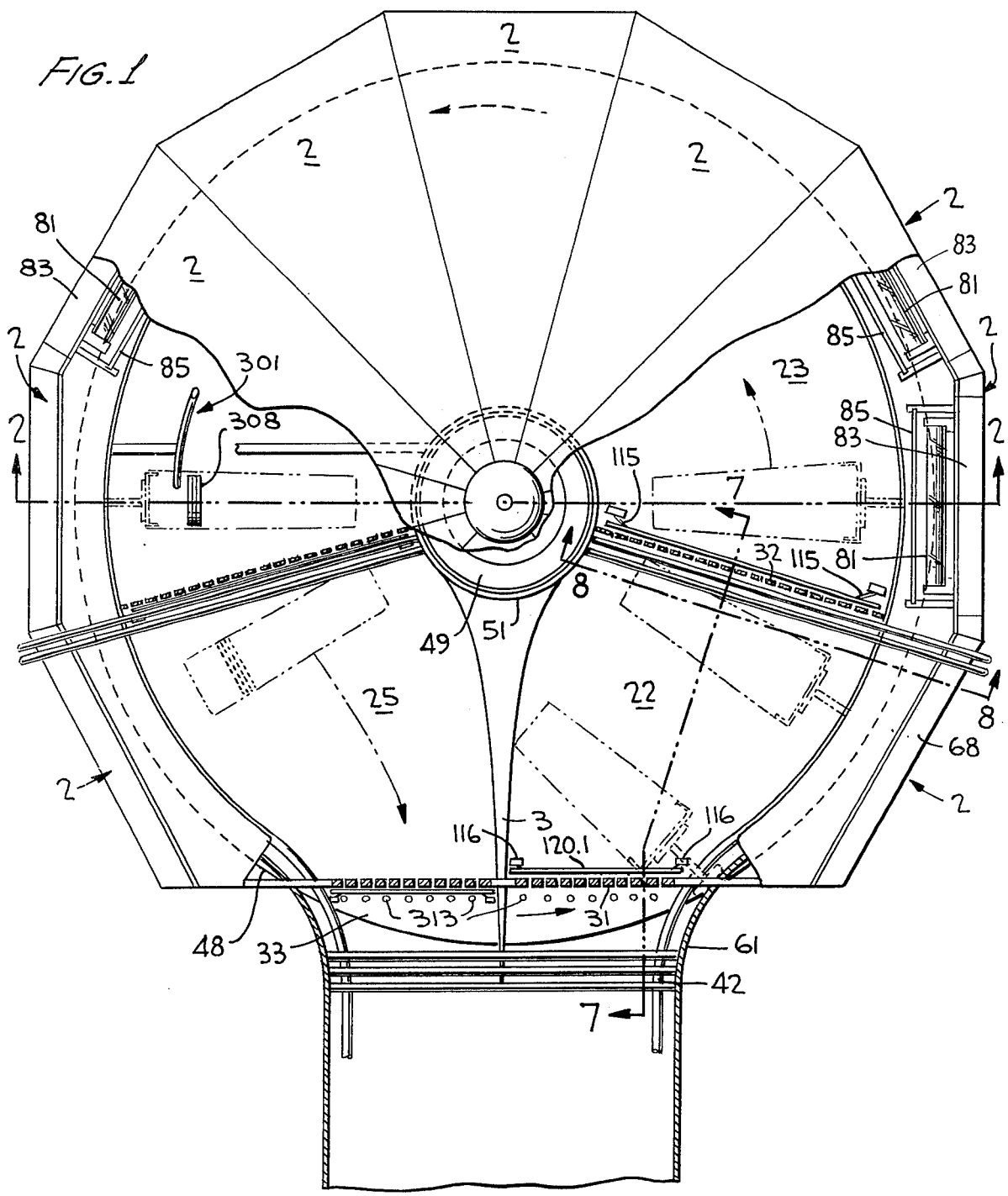
FIG. 1 is a top view, with certain sections broken away, of one embodiment of the apparatus utilized for performing the method of the present invention; p
Figure 6:
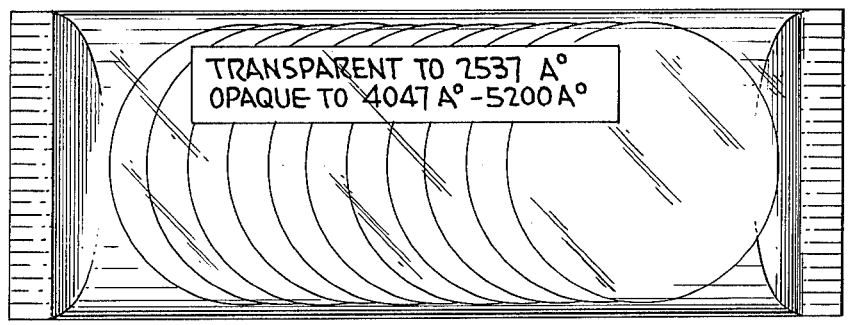
Figure 3:
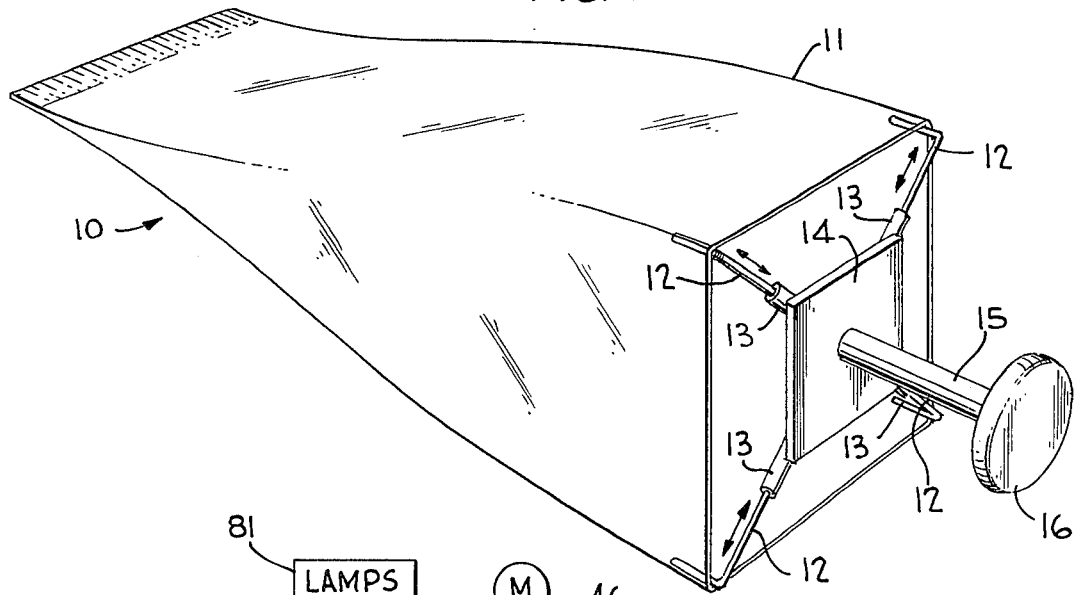
FIG. 3 is a perspective view of a container mounted on a holder having spring-biased fingers.
Figure 7:
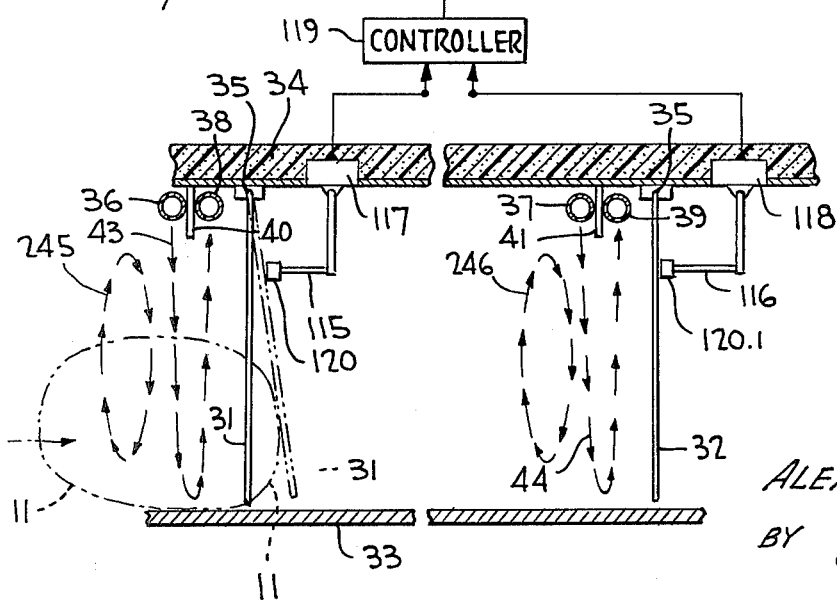

FIGS. 5a–5f schematically illustrate operations performed on the container of FIG. 3 while it is passing through the apparatus illustrated in FIGS. 1 and 2;

FIG. 6 is a top view of a packaged food product in accordance with the present invention;

FIG. 7 is a side sectional view taken through the line 7—7, FIG. 1, illustrating the ultraviolet isolation chamber in the embodiment of FIGS. 1 and 2;

FIG. 8 is a view taken through the line 8—8, FIG. 1, illustrating an air curtain in the embodiment of FIGS. 1 and 2;

FIG. 9 is a side sectional view of a second embodiment of the present invention; and FIG. 10 is a perspective view of the embodiment illustrated in FIG. 9.

In the detailed description of the present invention it is assumed that the food product being packaged is the usually highly perishable meat product known as bologna. The bologna is assumed to be in a commercially sterile condition, having just been apportioned and cooked, being at an elevated temperature of several hundred degrees Fahrenheit. It is to be understood, however, that the apparatus and method can be practiced with other food products which are in a commercially sterile, unfrozen condition.

Prior to being processed in accordance with the present invention, the sterile food product is placed in a plastic, laminated container or bag 11, FIG. 3. During apportionment and other handling operations from the time the product emerges from an oven until insertion in container, the surface of the product is exposed to certain bacteria colonies. It is generally the purpose of the invention to eliminate or render inert these colonies. To these ends, container 11 is preferably fabricated from gas impervious plastic laminations having a tendency to opacity (an opacity of approximately 80% or more) to visible light in the spectrum between 4,047 Angstroms and 5,200 Angstroms and having a tendency to transparency (a transparency of approximately 80% or more) to sterilizing ultraviolet radiation in the region of 2,537 Angstroms. By selecting the plastic films for bag 11 to be opaque to visible light energy in the 4,047–5,200 Angstrom region, stimulation of the growth of bacteria on the surface of the packaged food product through the action of necrohormones during storage at normal refrigerator temperatures is obviated. The container or bag 11 is fabricated from laminated plastic films to provide the least reactive surface between encapsulated inert gas and the food product within bag 11 after the bag has been sealed. The plastic laminated films of bag 11 provide a mechanical surface to the external environment that protects the food product from chemical reaction with oxygen in the air and abrasive damage. The plastic laminates forming the surface of container 11 are also of the type that are easily heat sealed to assure imperviousness of the interior of the container to the outside air after sealing. It has been found that laminated polyethylene films possess the desired optical sealing and protective properties sought for container 11.

Container 11, being formed as a bag, is sealed at one end and has, at its other end, an open mouth through which the product is inserted. After the product has been inserted into container 11 the mouth of the container is held open by holding assembly 10 that includes four spring fingers 12 for contacting the four corners of the open mouth of the bag. The ends of spring fingers 12 are bent by approximately 90° to form segments that extend along longitudinal seams of bag 11. Fingers 12 are fixedly mounted on the ends of stub rods 13 that extend radially from corners of square plate 14, located approximately in the center of the mouth of bag 11. Extending at right angles from the plane of plate 14 is shaft 15 that carries circular disc 16 at its end remote from plate 14. Disc 16 enables the food product to be conveyed in a controlled manner through a predetermined path of the food packaging to be described.

After the commercially sterile food product has been inserted in bag 11 and the spring fingers have been placed in situ against the corners of the bag, assembly 10 is ready to be placed in the food packaging apparatus of the present invention. In the embodiment illustrated in FIGS. 1, 2, 4, 7 and 8, assembly 10, FIG. 3, is fed to a rotating turntable-type conveyor by a belt conveyor (not shown) or the like. The packaging machine of this embodiment includes an entry section 21, an entry isolation section 22, a chamber 23 filled with inert gas and containing sterilizing ultraviolet radiation fields as well as sealing section 24, exit isolation section 25, and exit section 26. Each of sections 22 and 26, as well as chamber 23, is located within housing 1, having its walls, ceiling and floor fabricated from polyurethane of suitable thickness, approximately three inches to four inches, to enable a pneumatic seal to be formed thereby. Housing 1 is formed of a number of discrete annular segments 2, each having a straight line defining its exterior wall, for ease of manufacture. The inside ceiling and the far inside wall 37 of each of sections 2 are covered by stainless steel panels 91 and 92 to promote sterility and ultraviolet reflection whereby a uniform, ultraviolet field can be established in each of the sections of chamber 23. Segments 2 are bonded together by any suitable agent to form a pneumatic seal to prevent superatmospheric gas within housing 1 from escaping to the outside atmosphere, to minimize the amount of gas required.

To convey assemblies 10 between sections 21, 22, 25 and 26, and through chamber 23, rotary, horizontally disposed, circular turntable 33 is provided. Turntable 33 is driven by variable speed motor 46, the speed of which is controlled by network 47, through centrally located drive shaft 45 that extends through a vertically extending, centrally located bore of housing 1 and is journaled in the bore by bearings 46.1 that also provide a limited amount of sealing to prevent ready escape of the inert gas maintained at slightly greater than atmospheric pressure within the interior of housing 1. Turntable 33 is preferably fabricated of stainless steel because of the sterility, heat conduction and ultraviolet reflecting properties of stainless steel. The speed of motor 46 is determined by the nature of the food product being treated, depending upon the amount of time required for ultraviolet sterilization of the food product and the time required to displace oxygen within bag 11 with inert gas in chamber 23. Shaft 45 supports turntable 33 above circular plenum chamber 54 which is supplied with a cool dry inert gas (preferably nitrogen, carbon dioxide or a mixture thereof) by supply 53. Plenum chamber 54 is approximately coextensive in area with turntable 33 so that the upper surface of the turntable is cooled by conduction in response to the cool gas within the plenum chamber.

Assemblies 10 are conveyed to turntable 33 in entry section 21. Disc 16 of each assembly 10 rides in channel 41 that runs around the periphery of housing 1 from entrance section 21 to exit section 26, as well as from loading and unloading stations (not shown) outside of housing 1. Secured to opposed flanges of channel 41 are tubes 42 that run along the length of channel 41. Tubes 42 are separated from each other sufficiently to accept shaft 15 of assemblies 10. Channel 41 and tubes 42 constrain radial movement of assemblies 10 by virtue of the frictional engagement between them and disc 16. As turntable 33 rotates, assemblies 10 are rotated, with disc 16 of each assembly being dragged along through channel 41.

In entry section 21 the food product in assembly 10 begins to be cooled to a temperature slightly above the freezing point of water, approximately 36° F., the temperature of a typical refrigerator compartment. The temperature of gas in plenum chamber 54 is controlled to maintain this food product temperature regardless of the temperature of the product when it is placed on turntable 33, whereby for very hot products the gas temperature may be less than 0° F. and for cooler products close to 30° F.

Assemblies 10 are initially conveyed from entry section 21 to entry isolation section 22 which includes mechanical gates 31 and 32 that prevent ultraviolet radiation within chamber 23 from escaping to entrance region 21. The portions of gates 31 and 32 facing towards the interior of chamber 21 are ultraviolet absorbing, while the portion of gate 32 facing towards the interior of section 22 is an ultraviolet reflector. Each of gates 31 and 32 includes a multiplicity of elongated slats pivotably mounted by hinges 35 to ceiling 34 of the packaging machine, as illustrated in FIG. 7. The slats of gates 31 and 32 extend virtually to the upper surface of turntable 33. Gate 32 extends radially between the inner and outer walls of section 22 while gate 31 forms a chord from a point close to the outer tip of an arcuate, guiding wall of gas impervious, ultraviolet absorbing barrier 3 that separates sections 22 and 25 from each other, as well as sections 21 and 26 from each other. Gates 31 and 32 are spaced from each other by a distance greater than the normal distance between the sides of bag 11 after spring fingers 12 have been urged into place. Thereby, one of gates 31 or 32 is always in the path of ultraviolet radiation within chamber 23 so that the escape of ultraviolet radiation from the interior of the chamber to entry section 21 is prevented. The radiation blocking properties of chamber 22 are augmented by radiation absorbing properties of barrier 3 and the inwardly facing portion of outer wall 4 of chamber 22.

Isolation section 22 also includes a pair of gas curtains for preventing the escape of inert gas from chamber 23 to entrance section 21. The gas curtains are formed by jets of the inert gas within chamber 23 that is scavenged and led to tubes 36 and 37. Tubes 36 and 37 are positioned upstream of gates 31 and 32, respectively, in the direction of movement of assembly 10 on conveyor 33, and extend radially of section 22. Provided along the length of tubes 36 and 37 is a multiplicity of nozzle apertures for the inert gas. Respectively positioned slightly downstream of tubes 36 and 37 are return, apertured tubes 38 and 39 which receive the gas jets emitted by tubes 36 and 37 after the gas has been deflected from the floor of turntable 33. To prevent direct flow from the nozzles of tubes 36 and 37 back to the apertures of tubes 38 and 39, baffles 40 are provided between the individual tubes of the two air curtain assemblies.

As illustrated in FIG. 8, inert gas is supplied under pressure to tube 36 from section 62 of plenum 54 to form air curtain 43. To this end, tube 36 is connected to the outlet of pump 131, having an inlet that is connected to conduit 132, which is terminated in plenum section 62. Scavenged inert gas in section 62 is drawn through conduit 132 by pump 131 and emerges through the apertured nozzles of tube 36. The inert gas in the return stream flows through the apertures of tube 38 by suction established in tube 38 by pump 133. Inert gas sucked through the apertures of tube 38 is returned by pump 133 and conduit 134 to section 61 of plenum chamber 54. In the alternative, if there is a very high percentage of air in the return flow sucked through the apertures of tube 38, the outlet of suction pump 133 can be outgassed.

The gas curtains established by gas flowing from tube 36 to tube 38 and from tube 37 to tube 39 establish flow patterns as indicated by arrows 43 and 44, respectively; the gas curtains are occasionally denominated herein by the reference numerals 43 and 44. The inert gas flow patterns indicated by arrows 43 and 44 cause eddies to be formed in the atmospheric air, as indicated by the flow patterns shown by arrows 245 and 246, respectively. The eddy current air patterns 245 and 246 block the passage of atmospheric air to the interior of chamber 23, whereby the chamber can be considered as effectively filled with only the inert gas being fed thereto.

The cool inert gas that is recirculated over the top and bottom surfaces of disc 48 is derived from a suitable source, such as liquid nitrogen source 53, and is conveyed to plenum 54 beneath turntable 33 by conduit 55 and valve 56. Valve 56 is controlled to maintain the inert gas within chamber 23 at a predetermined temperature and pressure, whereby the food product is maintained at approximately 36° F., and is contacted with inert gas of approximately 1.1 atmospheres. The 1.1 atmosphere is maintained to assure displacement of air from bags 11 while they are in chamber 23 and to prevent bag rupture. To these ends, thermometer probe 87 and manometer 151 are mounted within chamber 23 to derive signals respectively indicative of the temperature and pressure of the inert gas in the chamber. These signals are fed to controller 152 that derives output signals for controlling the flow of inert gas into plenum 54 and out of chamber 23. Controller 152 responds to thermometer 87 and manometer 151 to solve, in effect, two simultaneous equations and derive control signals for the openings of valve 56 and bleed valve 153, that connects chamber 23 to a suitable sump.

To minimize condensation of water particles from the inert gas atmosphere on the food product and further to enhance the sterility of the inert gas in chamber 23, the water content of the gas is controlled by providing hygrometer 57 in plenum 54. Hygrometer 57 derives an output signal indicative of the amount of water in the atmosphere of plenum 54, which signal is supplied to controller 58. In response to the water content signal exceeding a predetermined level, controller 58 derives a control signal to open valve 153 whereby chamber 23 is completely purged to the sump connected to valve 153.

Plenum chamber 54 is divided into a pair of concentric sections 61 and 62, which sections are separated by an annular filter 63 which traps airborne particles in the inert gas. At the periphery of chamber 54 and turntable 33, ball bearing races 64 and 65 are provided for carrying ball bearings 66. Ball bearings 66 are separated from each other by a sufficient distance to enable inert gas within plenum 54 to pass radially from the periphery of the plenum through opening 67 provided between the periphery of disc 48 and the interior housing wall 68. Housing wall 68 is tapered inwardly, as indicated by reference numeral 69, immediately above the surface of turntable 33 to direct inert gas radially inwardly into the open mouth of bag 11 when the bag is within chamber 23. The inert gas flowing through opening 67 fills the interior of housing 68 within chamber 23 and flows back to the interior of plenum 54 through slot 51 between discs 48 and 49. To prevent leakage of the inert gas outside of plenum 54, sealing gaskets (not shown) extend radially of sections 22 and 25 between shaft 45 and the periphery of disc 48 beneath the surface of turntable 33.

Figure 5A:
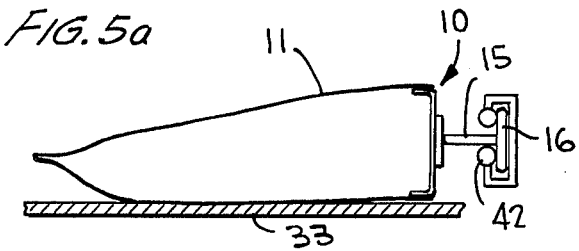
Figure 5B:
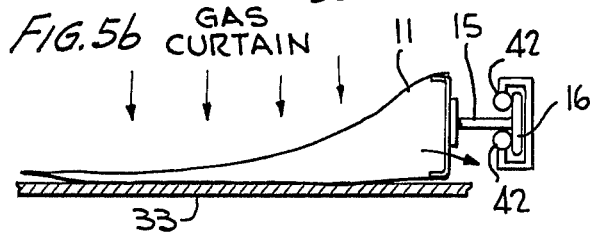
Figure 5C:
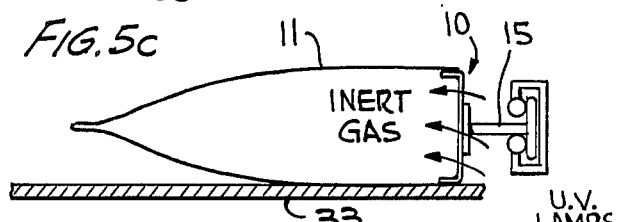

Assembly 10 is initially located on the floor of turntable 33 at entry station 21 so that radial movement of shaft 15 is constrained by channel 41 and tubes 42, as illustrated in FIG. 5a. Thereafter, turntable 33 rotates so assembly 10 proceeds through the gas curtain 43 and the gas curtain deflects bag 11 downwardly to compress it and cause a significant amount of atmospheric air within the bag to be forced from the interior of the bag, as illustrated in FIG. 5b. Bag 11 remains in a relatively decompressed state as it passes through entrance isolation chamber 22, and additional air is forced from the bag as it passes through gas curtain 44. After assembly 10 passes through gas curtain 44, the substantially radially directed inert gas jet passing through opening 67 passes through the open mouth of bag 11 and contacts the bologna therein, as illustrated in FIG. 5c. The inert gas within chamber 23 is maintained at a pressure of approximately 1.1 atmospheres, whereby atmospheric air remaining within bag 11 is quickly displaced and the surface of the food product is immersed in sterile, dry inert gas. The inert gas is maintained dry so that water vapor therein cannot condense on the surface of the food product; the inert gas, however, does not affect the amount of water in the product. After the initial rush of inert gas into the interior of bag 11 additional inert gas is continuously supplied to the food product within the interior of bag 11 as the bag rotates through chamber 23 until it arrives at sealing station 24. Thereby, virtually all atmospheric air within the interior of package 11 is displaced and an inert atmosphere is provided for the bologna within package 11 to provide the beneficial results of the present invention.

Figure 5D:
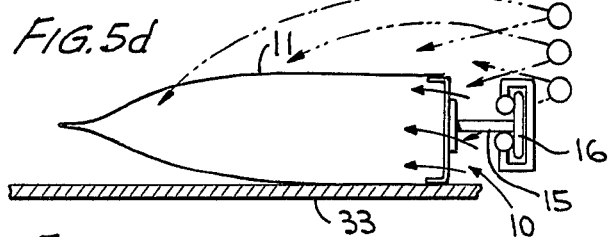
Figure 5E:
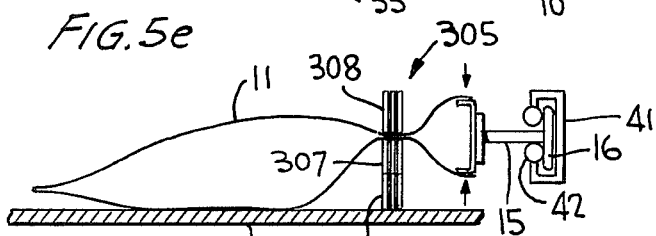
Figure 5F:
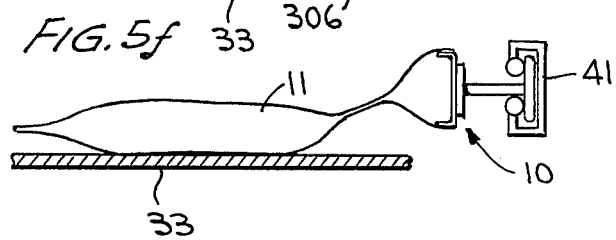
Figure 4:
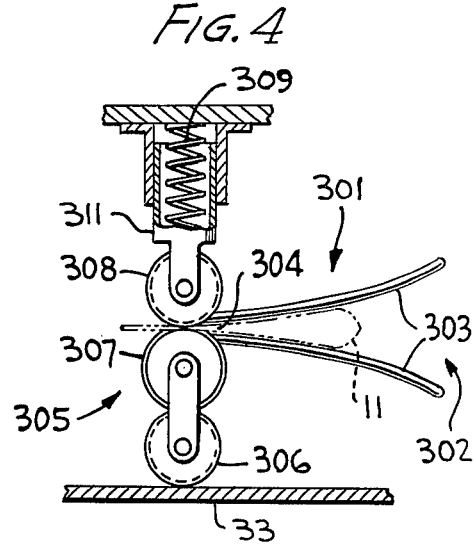
FIG. 4 is an enlarged view showing a portion of the sealing mechanism provided in the system of FIGS. 1 and 2.

Immediately after the initial rush of inert gas into the interior of bag 11 and while additional gas is being forced within the bag the food product in the bag is irradiated with sterilizing ultraviolet radiation, as indicated in FIG. 5d. The ulraviolet radiation has a wavelength of approximately 2,537 Angstroms and a dosage of approximately 26,400 microwatt seconds per square centimeter, a sufficient dosage at an appropriate wavelength to kill injurious organisms contained on the surface of the food product, as well as killing most atmospheric-borne bacteria, mold spores, yeast and viruses which may be present in the inert gases within chamber 23. Thereby, the ultraviolet radiation serves the dual purpose of sterilizing the inert gas which is encapsulated with the food product in bag 11 and killing bacteria on the surface of the food product.

The ultraviolet radiation source preferably comprises a multiplicity of ultraviolet emitting lamps 81 placed around the periphery of chamber 23 between gate 32 and sealing section 24. Tubes 81 are energized by suitable electrical power sources and lead lines (not shown) in a conventional manner and are mounted on fixture 82 that is fixedly mounted on removable outer wall 83 of the packaging system. Wall 83 is formed of a plurality of straight line segments, as illustrated by FIG. 1, which segments are fixedly connected to each other to form the sealed chamber 23. Wall segments 83, fixture 82 and ultraviolet tubes 81 are removable from the remainder of the housing for the machine in any suitable manner, such as wing nut and bolt assemblies 84. By mounting ultraviolet tubes 81 in proximity to the outer periphery of the housing for the machine on an easily removable wall, servicing of the tubes is facilitated so that they can be maintained at the working temperature which assures maximum radiation output.

To provide a seal for the interior of chamber 23 when ultraviolet tubes 81 and wall 83 are removed, the exterior surface of chamber 23 is formed of a window 85 that is transparent to ultraviolet radiation, preferably formed of Vycor glass. Window 85 is also preferably of the thermopane type to provide heat isolation from the interior of chamber 23 and lamps 81 so that the lamps can be operated at a temperature conducive to most efficient operation, 110° to 120° F. This temperature range is attained in response to heat generated by the lamps if they are in an enclosed housing. Because of the relatively cold atmosphere within chamber 23 and the higher temperature within housings for lamps 81, there is a tendency for moisture to condense on the surface of window 85. To prevent water vapor from condensing on window 85 a thermometer 86 is provided on each of the windows to function with temperature sensor 87 in the interior of chamber 23. The temperatures on the surface of window 85 and inside of chamber 23, as monitored by sensors 86 and 87, are compared in controller 88, which generates a signal to control the temperature of the window to a value slightly greater than the temperature of the gas within chamber 23. One system for maintaining the temperature of window 85 greater than that of the gas within the chamber is to control, in response to the output of controller 88, the amount of electric current supplied to heating coil 89 on window 85 to heat the window slightly above the temperature of the gas in chamber 23 and thereby prevent condensation from forming. In the alternative, valves (not shown) could be provided in an exterior wall of the housing for lamps 81 to ventilate the ultraviolet lamps to control the temperature thereof so that the temperature of window 81 is slightly greater than that of gas within chamber 23. Regardless of the system employed, condensation does not form on window 85 and ultraviolet radiation passes substantially unobstructed through window 85 to establish the required ultraviolet radiation field in chamber 23 to sterilize airborne particles in the inert gas and irradiate the food product in bag 11 which is transparent to the ultraviolet radiation generated by tubes 81. The ultraviolet radiation field or intensity within chamber 23 is rendered uniform by forming the walls of the chamber of a material that is highly reflective to ultraviolet radiation, as indicated supra. The ultraviolet radiation dosage supplied by lamps 81 to the food product can be varied, as required, in a number of ways, viz: by varying the speed of motor 46 that generally drives shaft 45 between one and three revolutions per minute and/or the number of ultraviolet lamps 81 energized.

After the food product within bag 11 has been irradiated by ultraviolet radiation and contacted with cool, dry inert gas for a sufficient time period to kill or render inert bacteria on the surface of the food product and to cause all of the atmospheric air within bag 11 to be displaced without affecting the hydration level of the food product, the bag and food product are carried by turntable 33 to sealing station 24. Sealing station 24 includes a V-shaped guide 301 positioned to intercept the portion of bag 11 in proximity to fingers 10 and a mouth 302 of sufficient size to enable the inflated bag to fit into it. Edges 303 of guide 301 are tapered vertically towards each other and extend in the direction of movement of bag 11 so that as the bag emerges from throat 304 of the guide portions of the top and bottom edges of the bag are virtually abutting against each other. Spring fingers 12 have sufficient resiliency and the portion of bag 11 engaged by guide 301 are such that bag 11 is virtually compressed to a flat state.

Downstream of throat 304 an electrically actuated plastic sealer 305 is located. Sealer is positioned right at throat 304 so that bag 11 travels through it in a compressed state and spring fingers 12 do not have an opportunity to reopen bag 11. Sealer 305 includes a drive wheel 306 which is frictionally coupled in driven relationship to turntable 33. Drive wheel 306 frictionally drives a second wheel 307 which is mounted above wheel 306, which in turn drives a third wheel 308. Wheel 308 includes an electric heater (not shown) so that its periphery is heated to a temperature sufficient to melt the surfaces of bag 11 with which it contacts to seal the bag. The shaft of wheel 308 is biased downwardly by spring 309 and bracket 310 to ensure pressure mating with the surface of the second wheel below it. The V guide 301 leads the edges of bag 11 to the conjunction of wheels 307 and 308, where the sides of bag 11 are engaged between the surfaces of drive wheel 307 and the heated wheel 308 to drive the bag between wheels 307 and 308, whereby the bag is heat sealed. Since wheel 306 derives its motive power from the surface of turntable 33, this arrangement ensures that bag 11 moves through the sealer 305 towards isolation chamber 25 at the same rate that turntable 33 is rotating.

After bag 11 has been sealed, assembly 10 including bag 11, spring fingers 12 and its mounting, is conveyed from sealing station 24 to exit isolation chamber 25. Exit isolation chamber 25 is identical to entrance isolation chamber 22, being provided with a pair of gas curtains for preventing the escape of inert gas from chamber 23, as well as a pair of gates which substantially prevent the escape of ultraviolet radiation from the interior of chamber 23. The gas and radiation curtains of exit chamber 25 are spaced from each other in the same manner as indicated supra with regard to entrance chamber 22. Exit chamber 25 is formed between ultraviolet absorbing surfaces of an arcuate wall of barrier 3 and the inwardly facing circumferential wall at the periphery of housing 1, whereby the same isolation characteristics are attained with both isolation chambers.

Both entrance and exit isolation chamber 22 and 25 are provided with means for stopping the packaging operation and for disconnecting power supplied to the ultraviolet lamps 81 in the event of a food product in bag 11 having a size greater than the size of the isolation chamber. Thereby, the escape of possibly harmful ultraviolet radiation from the interior of the chamber is prevented if both radiation shielding gates are simultaneously opened and the packaging operation is not allowed to proceed under conditions wherein the product is not irradiated by ultraviolet energy. An alarm can also be sounded in response to both of the radiation blocking gates of one of chambers 22 or 25 being simultaneously opened.

To sense simultaneous opening of radiation blocking gates 31 and 32, a pair of microswitches 115 and 166 is provided for each of gates 31 and 32, as illustrated in FIGS. 1 and 7. Microswitches 115 and 116 are respectively placed downstream of the slats of gates 31 and 32 by a distance commensurate with any one of the slats having been rotated by an amount whereby a relatively high level of ultraviolet radiation can escape through them. Microswitches 115 and 116 include horizontally mounted feelers that close normally open circuited contacts and are positioned at the inner and outer peripheries of chamber 22. Feelers of microswitches 115 and 116 are selectively engaged by contact bars 120 and 120.1, respectively mounted to be engaged by any of the slats of gates 31 or 32 being deflected by an amount to indicate that a relatively high radiation level is passing through the slat. In response to any of the slats being deflected sufficiently, contact bar 120 or 120.1 is deflected to engage contacts of microswitches 115 or 116 to close the corresponding switches.

Output leads from each of the switches 115 and 116 are connected to controller 119. In response to contacts or either of the switches 115 being closed at the same time as either of the switches 116 being closed, controller 19 derives a control signal to deenergize ultraviolet lamps 81 and motor 46. Thereby, the normally continuous rotation of turntable 33 is stopped and the ultraviolet field within chamber 23 is removed in response to gates 31 and 32 both opening simultaneously in response to a food product having dimensions greater than the dimensions of the isolation chamber 22. A further system for detecting the escape of ultraviolet energy from chamber 22 involves placing an array of ultraviolet detectors 313 in station 21, immediately upstream of gate 31. Array 313 extends across the length of gate 31 so that if more than a predetermined amount of ultraviolet energy escapes through any portion of the gate, a control signal is generated to stop motor 46 and shut off ultraviolet lamps 81. Similar operations occur in isolation chamber 25 in response to simultaneous deflection of gates thereof and escape of ultraviolet to a detector array included in section 26, and need not be described further.

After the food product has emerged from isolation chamber 25 it is conveyed (see FIG. 5f) to exit area 26, being guided by the arcuate wall of barrier 3. From exit area 26 assembly 10 is conveyed away from the packaging machine to a cutter (not shown) for cutting bag 11 between the seal and the portion engaging fingers 12. After bag 11 has been cut the spring finger assemblies are retrieved and reused.

The encapsulated food product emerging from exit station 26, in a typical embodiment wherein bologna is the food product, is illustrated in FIG. 6. The bologna is sealed in the inert sterile gas of approximately 1.1 atmosphere within plastic bag 11 that contains the radiation transmission properties described supra. The packaged bologna is preferably stored at a temperature slightly above the freezing point of water, such as 38° F., the approximate temperature of ordinary refrigerators. It has been found through actual experimentation that bologna packaged in accordance with the method of the present invention can be kept for in excess of three months in a refrigerated, nonfrozen state. This is in contrast with typical prior art packaging methods wherein bologna can be kept for generally no more than several days. It is to be understood that the method and apparatus can be practiced with food products other than bologna and has particular utility with regard to certain fresh fruits and vegetables and enables same to be preserved for three months or more without freezing or adverse affects on flavor, color or moisture content.

If servicing of the ultraviolet lamps 81 and space requirements for the apparatus are not particularly important, the turntable embodiment described supra can be replaced with a longitudinal conveyor, as illustrated in FIGS. 9 and 10. In the system illustrated by FIGS. 9 and 10, the rotary turntable 33 is replaced with a stainless steel conveying belt 231. Belt 231 carries an assembly 10 of the type illustrated by FIG. 3 through an elongated, rectangular housing 232 as illustrated in FIGS. 9 and 10. Housing 232 includes an entrance isolation chamber 233, a treating chamber 234 which is filled with an inert gas, a sterilizing ultraviolet radiation field and a sealing station 235. Downstream of chamber 234, an exit isolation chamber 236 is provided. Entrance and exit isolation chambers 233 and 236, as well as sealing station 235, are substantially the same as the corresponding stations in the previously described embodiment, whereby further description thereof is not deemed necessary.

Conveyor 231 extends on either side of housing 232 to provide entrance and exit stations where the food product and its encapsulating bag can be loaded thereon to be brought into housing 232 and can be removed from the conveyor for refrigeration and storage. Conveyor 231 is preferably a continuously driven endless belt that returns to the entrance of housing 232, on the left side thereof, by a path beneath or to the side of the housing.

Chamber 234 includes a plenum region 237 on the underside of belt 231 as the belt travels through the chamber 234. Inert, dry, cooled gas is supplied to plenum region 237 from a suitable source (not shown). The inert gas in plenum region 237 contacts the bottom surface of conveyor 231 to cool the conveyor and articles placed thereon by conduction. Inert gas from plenum 237 is also fed to apertures 239 in the side walls of housing 232 to cool the housing interior and enable the atmospheric air in the bags passing through the housing to be displaced. To this end, the inert gas pressure within housing 232 is superatmospheric, at approximately 1.1 atmospheres. The required pressure is attained by providing a manometer (not shown) in the interior of housing 232 and controlling a valve between plenum 237 and apertures 239 in response to the manometer reading. It is noted that the gas pressure maintaining system of FIGS. 9 and 10 is not recirculating so that purging of the system must generally be more frequent than with the system of FIGS. 1, 2, 7 and 8. The inert gas in chamber 234 above conveyor 231 is sterilized by sterilizing ultraviolet radiation fields generated by ultraviolet lamps 238 that are mounted in proximity to the ceiling of the chamber and extend substantially the length thereof. Ultraviolet tubes 238 irradiate the food product in bags 11 to sterilize the food product. As in the embodiment previously described, the interior walls of chamber 234 are fabricated with stainless steel panels to provide reflectivity for the ultraviolet radiation and uniform radiation fields within the chamber, as well as to promote food stability.

The apparatus illustrated in FIGS. 9 and 10 is provided with all of the controls described supra, whereby the temperature and pressure of the inert gas are maintained at a relatively constant level, the plenum is purged in response to the inert gas having an excessively high water content and condensation is prevented from forming on lamps 238. In addition, the speed of conveyor 231 can be controlled at will by varying the speed of a drive motor for the conveyor.

While there have been described and illustrated several specific embodiments of the invention, it will be clear that variations in the details of the embodiments specifically illustrated and described may be made without departing from the true spirit and scope of the invention as defined in the appended claims. For example, the method of the invention can be practiced by utilizing containers that are opaque to ultraviolet radiation as well as visible light radiation. In such an instance, the interior surface of the package is highly reflective to ultraviolet radiation, and the package is flooded by both ultraviolet radiation and the inert gas simultaneously through the open mouth of the bag. Thereafter the container is sealed as previously described while still within the chamber. Typical of such a package would be one formed of aluminum foil, constructed to be gas-tight under the expected pressures to be encountered with the inert gas.

I claim:

1. A method of packaging a food product in a substantially sterile condition comprising the steps of placing the substantially sterile product in a container which is sufficiently flexible as to be deformed by a current of gas, and which is opaque to visible light radiation, displacing any atmospheric air that is on the surface of the product with a dry, sterile, inert gas, sealing the container while said gas is substantially the only agent contacting the product and filling the container, and after the atmospheric air has been displaced irradiating the product with sterilizing ultraviolet lamp radiation while the gas is substantially the only agent contacting the surface of the product, the dosage of said ultraviolet radiation being sufficient to kill or render inert substantially all bacteria on the surface of the product, and maintaining only said gas in contact with the product surface from the time the gas initially displaces the air until the container is sealed, wherein the product is contacted with the inert gas by placing the container, while open, in an atmosphere of said gas, performing said irradiating and sealing steps in said atmosphere, and supplying a current of gas to the exterior of the container as the container enters said atmosphere, said current of gas compressing the container to force some of the atmospheric air from the interior of the container.

2. Apparatus for packaging food products comprising a chamber for receiving said products and enabling said products to be treated therein, means for supplying a dry, inert gas to said chamber, whereby any atmospheric air on the surface of the product is substantially displaced by the inert gas, said chamber including means for substantially preventing atmospheric air from entering the chamber and for enabling the chamber to be substantially filled with only said inert gas, a conveyor for transporting the food products while inside said chamber, a sterilizing ultraviolet radiation lamp having a field of radiation positioned to irradiate the food products while inside said chamber with sufficient dosage to kill or render inert substantially all bacteria on the surface of the product, and means located in the chamber positioned to be responsive to products on the conveyor for sealing a substantially sterile container in which the product is located while the product is inside the chamber, and wherein the means for preventing comprises a means for forming a curtain of said inert gas, said curtain being positioned so that the packaged food product passes through it.

3. Apparatus for packaging food products comprising a chamber for receiving said products and enabling said products to be treated therein, means for supplying a dry, inert gas to said chamber, whereby any atmospheric air on the surface of the product is substantially displaced by the inert gas, said chamber including means for substantially preventing atmospheric air from entering the chamber and for enabling the chamber to be substantially filled with only said inert gas, a conveyor for transporting the food products while inside said chamber, a sterilizing ultraviolet radiation lamp having a field of radiation positioned to irradiate the food products while inside said chamber with sufficient dosage to kill or render inert substantially all bacteria on the surface of the product, and means located in the chamber positioned to be responsive to products on the conveyor for sealing a substantially sterile container in which the product is located while the product is inside the chamber, further including means for substantially preventing ultraviolet radiation from escaping from within the chamber while allowing packaged food products to pass through the means for preventing ultraviolet radiation from escaping, which preventing means includes an isolation chamber having first and second ultraviolet absorbing gates through which the packaged food product passes, said gates being displaced from each other by a distance to enable a normal packaged food product to be located between them, and further including means for detecting when ultraviolet radiation is passing through both said gates simultaneously.

4. The apparatus of claim 3 further including means responsive to said detecting means for controlling movement of the conveyor.

5. The apparatus of claim 3 further including means responsive to said detecting means for controlling activation of the ultraviolet radiation source.

6. The apparatus of claim 3 wherein the detecting means includes means for detecting simultaneous mechanical movement of both said gates beyond predetermined points.

7. The apparatus of claim 3 wherein the detecting means includes means positioned downstream of both said gates for detecting ultraviolet radiation.

8. Apparatus for packaging food products comprising a chamber for receiving said products and enabling said products to be treated therein, means for supplying a dry, inert gas to said chamber, whereby any atmospheric air on the surface of the product is substantially displaced by the inert gas, said chamber including means for substantially preventing atmospheric air from entering the chamber and for enabling the chamber to be substantially filled with only said inert gas, a conveyor for transporting the food products while inside said chamber, a sterilizing ultraviolet radiation lamp having a field of radiation positioned to irradiate the food products while inside said chamber with sufficient dosage to kill or render inert substantially all bacteria on the surface of the product, and means located in the chamber positioned to be responsive to products on the conveyor for sealing a substantially sterile container in which the product is located while the product is inside the chamber, wherein the container is sufficiently flexible as to be deformed by a current of gas, the product being located in the container prior to entry into the chamber, and wherein the means for preventing comprises means for forming a curtain of said inert gas, said means for forming the curtain being positioned so that the container carrying a product passes through it while entering the chamber, said means for forming a curtain supplying a sufficient current of gas to the exterior of the container to compress the container to force atmospheric air in the container from the interior of the container through an opening in the container.

9. The apparatus of claim 8 wherein the inert gas supply means includes means for supplying the inert gas to the interior of the chamber and to the interior of the container through said opening.

10. Apparatus for packaging food products comprising a chamber for receiving said products and enabling said products to be treated therein, means for supplying a dry, inert gas to said chamber, whereby any atmospheric air on the surface of the product is substantially displaced by the inert gas, said chamber including means for substantially preventing atmospheric air from entering the chamber and for enabling the chamber to be substantially filled with only said inert gas, a conveyor for transporting the food products while inside said chamber, a sterilizing ultraviolet radiation lamp having a field of radiation positioned to irradiate the food products while inside said chamber with sufficient dosage to kill or render inert substantially all bacteria on the surface of the product, and means located in the chamber positioned to be responsive to products on the conveyor for sealing a substantially sterile container in which the product is located while the product is inside the chamber, wherein the inert gas supply means includes means for supplying the inert gas to the interior of the chamber through an opening in the container, and further including a plurality of spring fingers moving with the conveyor for urging each of said containers within the chamber to be open at said openings.

11. Apparatus for packaging food products comprising a chamber for receiving said products and enabling said products to be treated therein, means for supplying a dry, inert gas to said chamber, whereby any atmospheric air on the surface of the product is substantially displaced by the inert gas, said chamber including means for substantially preventing atmospheric air from entering the chamber and for enabling the chamber to be substantially filled with only said inert gas, a conveyor for transporting the food products while inside said chamber, a sterilizing ultraviolet radiation lamp source having a field of radiation positioned to irradiate the food products while inside said chamber with sufficient dosage to kill or render inert substantially all bacteria on the surface of the product, and means located in the chamber positioned to be responsive to products on the conveyor for sealing a substantially sterile container in which the product is located while the product is inside the chamber, wherein the source includes a surface transparent to said ultraviolet radiation, said surface forming a wall of said chamber and being susceptible to having condensation opaque to ultraviolet radiation forming thereon, and means for preventing condensation from forming on said surface.

12. The apparatus of claim 11 wherein said means for preventing condensation includes means for controlling the temperature of the surface.

13. Apparatus for packaging food products comprising a chamber for receiving said products and enabling said products to be treated therein, means for supplying a dry, inert gas to said chamber, whereby any atmospheric air on the surface of the product is substantially displaced by the inert gas, said chamber including means for substantially preventing atmospheric air from entering the chamber and for enabling the chamber to be substantially filled with only said inert gas, a conveyor for transporting the food products while inside said chamber, a sterilizing ultraviolet radiation lamp having a field of radiation positioned to irradiate the food products while inside said chamber with sufficient dosage to kill or render inert substantially all bacteria on the surface of the product, and means located in the chamber positioned to be responsive to products on the conveyor for sealing a substantially sterile container in which the product is located while the product is inside the chamber, further including a recirculating path for the inert gas in said chamber wherein the recirculating path includes a first surface of the conveyor opposite from a second surface of the conveyor in juxtaposition with the product, whereby said first surface is cooled in response to passage of the inert gas across it.

14. Apparatus for packaging food products comprising a chamber for receiving said products and enabling said products to be treated therein, means for supplying a dry, inert gas to said chamber, whereby any atmospheric air on the surface of the product is substantially displaced by the inert gas, said chamber including means for substantially preventing atmospheric air from entering the chamber and for enabling the chamber to be substantially filled with only said inert gas, a conveyor for transporting the food products while inside said chamber, a sterilizing ultraviolet radiation lamp having a field of radiation positioned to irradiate the food products while inside said chamber with sufficient disage to kill or render inert substantially all bacteria on the surface of the product, and means located in the chamber positioned to be responsive to products on the conveyor for sealing a substantially sterile container in which the product is located while the product is inside the chamber and further including means for controlling the supply of inert gas in response to the water content of gas in the chamber.

* * * * *